(12) United States Patent
Jorgensen et al.

(10) Patent No.: US 10,255,478 B2
(45) Date of Patent: Apr. 9, 2019

(54) FULL RESOLUTION COLOR IMAGING OF AN OBJECT

(71) Applicant: Ortho-Clinical Diagnostics, Inc., Raritan, NJ (US)

(72) Inventors: Jens H. Jorgensen, Rochester, NY (US); Michael W. LaCourt, Spencerport, NY (US); Donald J. Moran, Jr., Rochester, NY (US); David J. Hawks, Rochester, NY (US); Joseph Wycallis, Pittsford, NY (US); Stephen C. Arnold, Honeoye Falls, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 804 days.

(21) Appl. No.: 14/730,437

(22) Filed: Jun. 4, 2015

(65) Prior Publication Data

US 2015/0269412 A1    Sep. 24, 2015

Related U.S. Application Data

(62) Division of application No. 13/654,686, filed on Oct. 18, 2012, now Pat. No. 9,066,021.

(51) Int. Cl.
*G01N 33/50* (2006.01)
*G06K 9/00* (2006.01)
(Continued)

(52) U.S. Cl.
CPC ....... *G06K 9/00134* (2013.01); *G01N 21/255* (2013.01); *G01N 21/82* (2013.01);
(Continued)

(58) Field of Classification Search
None
See application file for complete search history.

(56) References Cited

U.S. PATENT DOCUMENTS 3,971,065 A    7/1976  Bayer
5,398,066 A    3/1995  Martinez-Uriegas et al.
(Continued)

FOREIGN PATENT DOCUMENTS

CN    101039437 A    9/2007
EP       0864858 B1    9/1999
(Continued)

OTHER PUBLICATIONS

Notification of Reasons for Refusal issued in Japanese Patent Application No. 2013-216118 dated Jun. 27, 2017.
(Continued)

*Primary Examiner* — Christopher L Chin
(74) *Attorney, Agent, or Firm* — K&L Gates LLP; Louis C. Cullman; Brian J. Novak (57) ABSTRACT

The invention relates generally to both a method and apparatus for the creation of full resolution color digital images of diagnostic cassettes or objects of interest using a grayscale digital camera or sensor combined with time sequential illumination using additive primary colors followed by post exposure digital processing. Such procedures and equipment is of significant economic value when employed in situations such as diagnostic clinical analyzers where space is limited and image quality requirements are high.

13 Claims, 9 Drawing Sheets

Sequential Color Imaging Apparatus Diagram (51) Int. Cl.

| | |
|---|---|
| *H04N 5/235* | (2006.01) |
| *G01N 21/82* | (2006.01) |
| *H04N 5/225* | (2006.01) |
| *G02B 27/02* | (2006.01) |
| *G01N 21/25* | (2006.01) |
| *G06T 7/00* | (2017.01) |
| *G06T 11/00* | (2006.01) |

(52) U.S. Cl.
CPC ......... *G02B 27/024* (2013.01); *G06K 9/0014* (2013.01); *G06T 7/0012* (2013.01); *G06T 11/001* (2013.01); *H04N 5/2256* (2013.01); *H04N 5/2354* (2013.01); *G06T 2207/10024* (2013.01); *G06T 2207/10152* (2013.01); *G06T 2207/20216* (2013.01); *G06T 2207/30004* (2013.01)

(56) References Cited

U.S. PATENT DOCUMENTS

| | | | |
|---|---|---|---|
| 5,430,395 | A | 7/1995 | Ichimaru |
| 5,594,808 | A | 1/1997 | Shen |
| 5,620,898 | A | 4/1997 | Yaremko |
| 5,767,407 | A | 6/1998 | Sinha |
| 5,768,407 | A | 6/1998 | Shen |
| 2003/0169347 | A1 | 9/2003 | Jenkins |
| 2007/0211460 | A1 | 9/2007 | Ravkin |
| 2008/0088858 | A1* | 4/2008 | Marcu ............... H04N 1/407 358/1.6 |
| 2010/0007588 | A1 | 1/2010 | Zygmunt |
| 2011/0176029 | A1 | 7/2011 | Boydston |
| 2012/0281111 | A1* | 11/2012 | Jo ..................... H04N 5/217 348/229.1 |
| 2013/0088031 | A1 | 4/2013 | Jones |

FOREIGN PATENT DOCUMENTS

| | | | |
|---|---|---|---|
| JP | 59-214010 | A | 12/1984 |
| JP | 3-75561 | A | 3/1991 |
| JP | 8-79773 | A | 3/1996 |
| JP | 10-190942 | A | 7/1998 |
| JP | 2004-208000 | A | 7/2004 |
| JP | 2011-125026 | A | 6/2011 |
| JP | 2012-94967 | A | 5/2012 |
| WO | 1998/000980 | A1 | 1/1998 |

OTHER PUBLICATIONS

Getting Started with MATLAB® 7, (2007).
European Search Report—dated Jul. 14, 2014—13189153.3.
Ariana, D. et al., "Integrating multispectral reflectance and fluorescence imaging for defect detection on apples", Computers and Electronics in Agriculture, Feb. 1, 2006, p. 148-161, vol. 50, Issue 2, Elsevier, Amsterdam, NL.
Bouchard, Matthew B. et al., "Ultra-fast multispectral optical imaging of cortical oxygenation, blood flow, and intracellular calcium dynamics", Optics Express, OSA, Aug. 31, 2009, p. 15670-15678, vol. 17, Issue 18, Washinaton DC (US).
Brydegaard, Mikkel et al., "Broad-band multispectral microscope for imaging transmission spectroscopy employing an array of light-emitting diodes". American Journal of Physics, Feb. 1, 2009, p. 104-110, vol. 77, Issue 2.
Chaudhari, Abhijit J. et el., "Excitation spectroscopy in multispectral optical fluorescence tomography: methodology, reasibility and computer simulation studies", Physics in Medicine and Biology, Aug. 7, 2009, p. 4687-4704, vol. 54, Issue 15, Bristol GB.
Du, Hao et al., "A prism-based system for multispectral video acquisition", 2009 IEEE 1210 International Conference on Computer Vision, Sep. 29, 2009, p. 175-182, Kyoto.
Levenson, Richard M., et al., "Multispectral imaging in biology and medicine: Slices of life", Cytometry Part A, Aug. 1, 2006, p. 748-758, vol. 69A, Issue 8.
Levenson, R. M., et al., "Multiplexing with Multispectral Imaging: From Mice to Microscopy", ILAR Journal, Jan. 1, 2008, p. 78-88, vol. 49, Issue 1.
Tominaga, Shoji, et al., "Spectral imaging by synchronizing capture and illumination", J. Opt. Soc. Am. A, Sep. 2012, p. 1764-1775, vol. 29, Issue 9.
First Office Action in English and Chinese issued in Chinese Patent Application No. 201310491905.9 dated Aug. 3, 2016.
Office Action issued in related Japanese Patent Application No. 2013-216118 dated May 15, 2018 and English translation of same.
EIAJ Test Chart A, EIAJ-Test patterns, Japan, Dai Nippon Printing Co., Ltd., Electronic Device Division [retrieved on Jul. 21, 2006], Internet:<URL: http://www.dnp.co.jp/semi/j/test/a_pattern.html>. 1 page.
Notice of Reexamination issued in related Chinese Patent Application No. 201310491905.9 and English translation of same.

* cited by examiner

Fig. 1 – Sequential Color Imaging Apparatus Diagram

Fig. 2 – Sequential Illumination Process

Fig. 3 – Image Reconstruction Process

Fig. 4 – Field of View of the Digital Camera or
Sensor Showing the Diagnostic Cassette Fig. 5 – Exemplary LED Spectrums Fig. 6 – Cassette IlluminationDiagram
(Plan View)

Fig. 7 – Detail of Front Illumination Light Emitting Diode Circuit Board

Fig. 8 – Detail of Back Illumination Light Emitting Diode Circuit Board

Fig. 9 – MatLab Digital Image Processing M-File

```
clear all
front_BLUE  = imread('f:\BV_Front_Blue.bmp');
front_GREEN = imread('f:\BV_Front_Green.bmp');
front_RED   = imread('f:\BV_Front_Red.bmp');
back_BLUE   = imread('f:\BV_Back_Blue.bmp');
back_GREEN  = imread('f:\BV_Back_Green.bmp');
back_RED    = imread('f:\BV_Back_Red.bmp');
```
⎬ 901

```
rows = size(front_BLUE, 1);
cols = size(front_BLUE, 2);
```
⎬ 902

```
depth = 3;

front_RGB = zeros(rows, cols, depth);
back_RGB  = zeros(rows, cols, depth);
```
⎬ 903

```
scalar_weights   = [0.35 0.35 0.30]';
weights          = imread('f:\weights.bmp');
```
⎬ 904

```
for i = 1:1:rows
    for j = 1:1:cols
        front_RGB(i,j,1) = scalar_weights(1).*weights.*front_RED(i,j);
        front_RGB(i,j,2) = scalar_weights(2).*weights.*front_GREEN(i,j);
        front_RGB(i,j,3) = scalar_weights(3).*weights.*front_BLUE(i,j);
        back_RGB(i,j,1)  = scalar_weights(1).*weights.*back_RED(i,j);
        back_RGB(i,j,2)  = scalar_weights(2).*weights.*back_GREEN(i,j);
        back_RGB(i,j,3)  = scalar_weights(3).*weights.*back_BLUE(i,j);
    end
End
```
⎬ 905

```
maxFront = max(max(max(front_RGB)));
maxBack  = max(max(max(back_RGB)));
```
⎬ 906

```
figure(1), imagesc(front_RGB/maxFront);
figure(2), imagesc(back_RGB/maxBack);
```
⎬ 907

FULL RESOLUTION COLOR IMAGING OF AN OBJECT

CROSS REFERENCE TO RELATED APPLICATIONS

This application is a divisional application of U.S. Non-Provisional application Ser. No. 13/654,686 filed Oct. 18, 2012, which claims priority and is hereby incorporated by reference in their entirety.

FIELD OF THE INVENTION

The invention relates generally to both a method and apparatus for the creation of full resolution color digital images of diagnostic cassettes or an object of interest using a gray-scale digital camera or sensor. In particular, the invention more generally relates to both a method and apparatus for analyzing solutions such as blood samples, and more specifically, to such methods and apparatus that analyze blood samples by detecting and quantifying agglutinates formed in those samples in response to immunological reactions. Even more particularly, the invention relates to an automated system and method for analyzing blood samples in this way.

BACKGROUND OF THE INVENTION

Immunological agglutination reactions are used for identifying various kinds of blood types and for detecting various kinds of antibodies and antigens in blood samples and other aqueous solutions. In a conventional procedure, a sample of red blood cells is mixed with serum or plasma in test tubes or microplates, and the mixture may then be incubated and centrifuged. Various reactions either occur or do not occur depending on, for example, the blood type of the red blood cells or whether certain antibodies are present in the blood sample. Typically, these reactions manifest themselves as binding of cells or particles with antigens or antibodies on their surfaces, referred to as agglutinates. Thus, the absence of any such clumps indicates that no reaction has occurred; and the presence of such clumps indicates that a reaction has occurred, with the size and amount of such clumps being a quantitative indicator of the level or concentration in the sample, or an indicator of the reaction strength, affinity of the complex for which the blood sample was tested.

A traditional agglutination test method, referred to as column agglutination technology, is presently available (as disclosed in U.S. Pat. No. 5,594,808 which is hereby incorporated by reference in its entirety). Column agglutination technology is defined as the analysis of blood and blood products utilizing filtration as a means of separating agglutinated, precipitated, absorbed or adsorbed particulate components from non-reactive components for immunoassay applications. In this method, gel or glass bead microparticles are contained within a small column, referred to as a microcolumn. A reagent, such as anti-A, is dispensed in a diluent in the microcolumn and test red blood cells are placed in a reaction chamber above the column. The column, which is typically one of a multitude of columns formed in a transparent cassette, is centrifuged. The centrifuging accelerates the reaction, if any, by drawing the red blood cells through the reagent to enhance the agglutination, and subsequently urges any unbound cells to the bottom of the column. The glass beads or gel in the microcolumn act as a filter and resist or impede downward movement of the particles in the column. As a result, the nature and distribution of the particles in the microcolumn after centrifuging provides a visual indication of whether any agglutination reaction occurred in the microcolumn, and if so, of the strength of that reaction.

In particular, if no agglutination reaction occurs, then all or virtually all of the red blood cells in the microcolumn pass downward, during centrifuging, to the bottom of the column and form a pellet at that bottom. If there is a very strong reaction between the reagent and the red blood cells, virtually all of the red blood cells agglutinate, and large agglutinates form at the top of the microcolumn, above the gel or glass beads contained therein. The gel or glass beads prevent the agglutinates from passing, during centrifuging, to the bottom of the column, so that after centrifuging the agglutinates remain on the surface of the gel or beads.

If there is a reaction between the reagent and the blood cells, but this reaction is not as strong as the above-described very strong reaction, then some but not all of the red blood cells agglutinate. The percentage of red blood cells that agglutinate and the size of the agglutinated particles both vary directly with the strength of the reaction. During centrifuging, the unreacted blood cells pass to the bottom of the column, and the distance that the agglutinated particles pass downward through the column depends on the size and number of those particles. Hence, the size of the pellet of red blood cells at the bottom of the microcolumn, and the extent to which the agglutinates penetrate into the gel or glass beads in the microcolumn, are both inversely related to the strength of the reaction between the reagent and the red blood cells.

With some column agglutination technology analyzers, after the desired processing steps have been performed, the microcolumn is observed, or read, by a human operator, who then classifies the reaction between the reagent and the red blood cells. Conventionally, the reaction is classified as either negative or positive; and if positive, the reaction is then further classified into one of four classes depending on the strength of the reaction.

Conventional blood analysis systems (as disclosed in U.S. Pat. No. 5,620,898 which is hereby incorporated in its entirety by reference) include a multitude of stations or assemblies or subsystems, each of which performs one or more functions, and typically a significant amount of operator supervision and labor is needed to operate the systems. In this application, an imaging analysis subsystem is disclosed which allows a high quality image of a diagnostic cassette or an object of interest to be obtained which can be analyzed in an automated manner so that an appropriate analytical result is obtained without operator intervention. One automated method comprises the steps of producing an illuminated monochromatic digital image of the microcolumn on an array of pixels, and assigning to each pixel in the illuminated image, a data value representing the intensity of the illuminated image on the pixel. These data values are then processed according to a predetermined program to determine if an agglutination pattern is present and, if so, to classify that pattern into one of a plurality of predefined classes. Another automated method disclosed herein comprises the steps of producing multiple illuminated monochromatic images of the microcolumn on an array of pixels, and assigning to each pixel in the illuminated image, a data value representing the intensity of the illuminated image on the pixel. These data values are then processed according to a predetermined program to construct a color digital image which is then used to determine if an agglutination pattern is present and, if so, to classify that pattern into one of a plurality of predefined classes. In both of the processing procedures above, the pixel array is separated into a plurality of zones, and the data values for the pixels in each zone are processed according to a respective predetermined procedure to determine values for a predefined set of variables. Then, those determined values are processed to determine whether an agglutination pattern is present in the solution, and if so, to classify that pattern into one of the predefined classes.

The solutions are contained in a column having glass microbeads or gel. The image processing program searches the location of the column in the source image on the pixel array; and after the column is located, the program generates a window to cover the column where the red cells are located. The program then selects three reference regions from inside and outside the column and measures the intensity or gray levels in these regions, and these measured gray levels are used to determine certain threshold values that are subsequently used in the processing program.

For the feature calculation, the bead/gel column is divided into five different zones. The region on top of the bead/gel column is defined as the positive zone, the region at the bottom of the column is defined as the negative zone, and the area between the positive and negative zones is separated into three intermediate zones (also considered to be "positive zones"). The red cells located in the positive zones are extracted using a threshold method, and the red cell agglutinates located in the intermediate zones are extracted using a morphological filter. In addition, the balance of the red cells between the left and right sides of the column is determined. For each column, the above parameters are preferably calculated for both front and back side images of the column, and the two calculated values for each parameter are combined. The agglutination reaction is then classified on the basis of these combined features. An algorithm for the evaluation of the column agglutination results is disclosed by Jian Shen, Mykola Yaremko, Rosemary Chachowski, Josef Atzler, Thierry Dupinet, Daniel Kittrich, Hansjoerg Kunz, Karl Puchegger, and Reiner Rohlfs in U.S. Pat. No. 5,594,808 entitled "Method and system for classifying agglutination reactions" and by Jian Shen, Mykola Yaremko, Rosemary Chachowski, Josef Atzler, Thierry Dupinet, Daniel Kittrich, Hansjoerg Kunz, Karl Puchegger, and Reiner Rohlfs in U.S. Pat. No. 5,768,407 entitled "Method and system for classifying agglutination reactions" both of which are hereby incorporated by reference in their entirety.

Some of the advantages of the invention disclosed herein lies in the use of a gray-scale digital camera or sensor as compared to a conventional color digital camera or sensor which require the application of superimposed color filter arrays. Color filter arrays (as disclosed in U.S. Pat. No. 3,971,065 which is hereby incorporated in its entirety by reference), when producing a color digital image of a specified output spatial resolution, require the use of interpolation algorithms which reduces the effective resolution of the color digital image that results. The reduced resolution color digital image so produced causes a decrease in the specificity of the column agglutination algorithm described above making the outcome of the test less certain. Alternatively, one could employ a color digital camera or sensor that uses color filter arrays such that an output full resolution color digital image is produced. However, that would require a digital sensor having a physically larger sensor (more rows and columns of pixels) such that when used in conjunction with a color filter array and the associated interpolation algorithm that the color digital image so produced would be of equivalent full resolution. The drawback in using this latter method being increased cost and a longer optical imaging path, the longer imaging path being required to obtain an equivalent depth of field when compared to the invention disclosed herein.

SUMMARY OF THE INVENTION

One object of the invention is to overcome the disadvantages of the known art described above and to achieve one or more of the objectives described below.

An object of the invention disclosed herein is to provide an economic advantage when taking images of diagnostic cassettes or objects of interest where space is limited and image quality requirements are high.

Yet, another object of the invention disclosed herein is to provide the ability to produce color digital images of diagnostic cassettes or objects of interest at full sensor resolution using only a gray-scale digital camera or sensor.

Still, another object of the invention disclosed herein is to provide the ability to produce color digital images of diagnostic cassettes or objects of interest at full sensor resolution at reduced cost.

Yet, another object of the invention disclosed herein is to provide the ability to produce color digital images of diagnostic cassettes or objects of interest at full sensor resolution having improved quality over color digital images produced using color digital cameras or sensors of equivalent spatial resolution employing color filter arrays.

The foregoing and further objects of the invention are accomplished accordingly where one aspect of the invention described herein is an color digital apparatus for the construction of a color digital image of an object of interest comprising, a gray-scale digital camera or sensor capable of forming an image based upon a single exposure to illuminated objects, a mechanical means to hold said diagnostic cassette or object of interest to be imaged during imaging, a source of front illumination capable of multiple illuminations of said object to be imaged with red, green, and blue wavelength light, a source of rear illumination capable of multiple illuminations of said object to be imaged with red, green, and blue wavelength light and a means to construct a color digital image of said object to be imaged wherein said means is in electrical contact with said gray-scale digital camera or sensor.

Another aspect of the invention disclosed herein is a method of constructing a monochrome digital image of a diagnostic cassette or an object of interest comprising, optically obtaining a red, green, and blue color plane of image data using a gray-scale digital camera or sensor, selecting one color plane for subsequent manipulation, multiplying, element by element, said selected color plane by a pre-defined red weighting matrix producing a weighted selected color plane, and multiplying said weighted selected color plane by a pre-defined selected gain scalar producing a final selected color plane.

Yet, another aspect of the invention described herein is a method of determining the presence or absence of an agglutination reaction in an imaged diagnostic cassette or object of interest using a combination of at least one red, green, or blue monochrome digital image.

A further aspect of the invention described herein is to provide a method of constructing a color digital image of an object of interest comprising, optically obtaining a red color plane of image data using a gray-scale digital camera or sensor, optically obtaining a green color plane of image data using a gray-scale digital camera or sensor, optically obtaining a blue color plane of image data using a gray-scale digital camera or sensor, multiplying, element by element, said red color plane by a pre-defined red weighting matrix producing a weighted red color plane, multiplying said weighted red color plane by a pre-defined red gain scalar producing a final red color plane, multiplying, element by element, said green color plane by a pre-defined green weighting matrix producing a weighted green color plane, multiplying said weighted green color plane by a pre-defined green gain scalar producing a final green color plane, multiplying, element by element, said blue color plane by a pre-defined blue weighting matrix producing a weighted blue color plane, multiplying said weighted blue color plane by a pre-defined blue gain scalar producing a final blue color plane, and combining said final red color plane, said final green color plane, and said final blue color plane into said color digital image of said object of interest.

A further aspect of the invention disclosed herein is that the smaller physical size of the gray-scale digital imager when compared to a digital camera or sensor of equivalent resolution employing color filter arrays which results in a shorter and more compact optical path suitable for confined spaces.

Yet, still another aspect of the invention disclosed herein is to enable a calibration procedure that is responsive to electrical component variability, to variations in camera sensitivity, to variations in ambient lighting, to variations in power input, to variations in required image contrast, to degradations in electrical components over time, to electrical component temperature sensitivity, and to variations in component changes due to replacement or change in component manufacturer.

Further objects, features, and advantages of the present application will be apparent to those skilled in the art from detailed consideration of the embodiments that follow.

BRIEF DESCRIPTION OF THE DRAWINGS

FIG. 2 is a schematic diagram of the sequential exposure and imaging process. At Time 1, a red light source 200 is used to illuminate a color object 203, from both the front and the back, resulting in a combination reflection and transmission intensity plane 204. At Time 2, a green light source 201 is used to illuminate a color object 203, from both the front and the back, resulting in a combination reflection and transmission intensity plane 205. At Time 3, a blue light source 202 is used to illuminate a color object 203, from both the front and the back, resulting in a combination reflection and transmission intensity plane 206.

FIG. 3 is a diagram of the color reconstruction process. Individual intensity values from the red color plane 204 is combined with the individual intensity values from the green color plane 205 and the individual intensity values from the blue color plane 206 to produce a color image 300.

DETAILED DESCRIPTION OF THE PREFERRED EMBODIMENT

While the present invention is described with respect to the preferred embodiments described below and shown in the figures, the present invention is limited only by the metes and bounds of the claims that follow.

The apparatus and methods described herein enable the creation of a color digital image of preferably full resolution using a gray-scale digital camera or sensor 100.

The benefits of the apparatus include a reduced unit manufacturing cost when compared to the equivalent process using a full color digital camera or sensor and no reduction in image quality due to the use of a color filter array to produce a color image. Another important benefit is the use of a gray-scale digital camera or sensor 100 allows for a shorter and more compact optical path suitable for confined spaces.

For a general understanding of the disclosed technology, reference is made to the drawings. In the drawings, like reference numerals have been used to designate identical elements. In describing the disclosed technology, the following term(s) have been used in the description.

The term "image" or "picture" refers to a two-dimensional light intensity function optionally having x-axis and y-axis position coordinates with a numerical value that is proportional to the brightness or gray level of the image at the specified coordinate point.

The term "analog" or "analogue" refers a picture or image that is continuous both spatially in two-dimensions and in brightness or intensity.

The term "digital" refers a picture or image that is digitized to a predefined number of levels both spatially in two-dimensions and in brightness or intensity. A digital image may be represented by a vector or matrix whose row and column indices identify a point in the image and the corresponding vector or matrix numerical value identifies the brightness or intensity at that point.

The term "intensity" refers to the amount of light reaching a digital camera or sensor such that the higher the relative output value the greater the number of photons reaching the digital camera or sensor. Intensity is commonly associated with digital pictures or images.

The term "density" refers to the amount of light reaching a digital camera or sensor such that the higher the relative output value the fewer the number of photons reaching the digital camera or sensor. Density is commonly associated with photographic pictures or images.

The term "reflection intensity" refers to the amount of light received by a digital camera or sensor where the light path originates at a source and reverberates or bounces or is reflected off an object of interest, subsequently arriving at the digital camera or sensor.

The term "transmission intensity" refers to the amount of light received by a digital camera or sensor where the light path originates at a source and proceeds through an object of interest, subsequently arriving at the digital camera or sensor.

The term "contrast" refers to the difference in the color and brightness of the object and other objects within the same field of view. The maximum contrast of an image is the contrast ratio or dynamic range.

The term "dynamic range" or equivalently "contrast ratio" refers to the ratio of the luminance of the brightest color (white) to that of the darkest color (black) that the system is capable of producing.

The term "luminance" refers to a photometric measure of the intensity per unit area of light travelling in a given direction. It describes the amount of light that passes through or is emitted from a particular area, and falls within a given solid angle.

The term "red" refers the color perceived by humans corresponding to the longer wavelengths of visible light, generally in the wavelength range of substantially 630-740 nanometers.

The term "green" refers the color perceived by humans corresponding to visible light having a spectrum dominated by energy generally with a wavelength of substantially 520-570 nanometers.

The term "blue" refers the color perceived by humans corresponding to the shorter wavelengths of visible light, generally in the wavelength range of substantially 440-490 nanometers.

The term "monochrome" refers to images in one color or shades or tones of one color. A black-and-white image, composed of shades of gray, is an example of a monochrome image.

The term "gray-scale" refers to a digital image in which the value of each pixel is a single sample, that is, it carries only intensity information. Images of this sort, for example, black-and-white, are composed exclusively of shades of gray, varying from black at the weakest intensity to white at the strongest intensity.

The term "plane" or "color plane" refers to a set of intensities or densities associated with a single color which may be the result of a reflection process, transmission process, or a combination of both.

The term "pixel" refers to a discrete spatial component of a digital picture or image and is short for picture element.

The term "full resolution" refers to a monochrome or color digital image having maximum information content associated a specified number of pixels where, for example, a rectangular digital image the total number of pixels is the number of rows of pixels multiplied by the number of columns of pixels.

The term "reduced resolution" refers to a monochrome or color digital image where the information content has been reduced by the application of a mathematical algorithm to the raw pixel data, such as interpolation or low pass filtering, which has been used to generate output pixel values. While the number of pixels in the reduced resolution digital image may be spatially the same as a full resolution digital image, that is the spatial size of the two digital images are the same, the information content of the reduced resolution digital image is significantly lower.

The term "spatial resolution" refers to the physical size or dimensions of a digital image. For a rectangular digital image, the spatial resolution is the number of pixels in a row by the number of pixels in a column. The common unit of resolution for digital cameras or sensor is megapixels.

The term "suitably capture" or "suitably captured" refers to methods that enable obtaining high quality imagery of diagnostic cassettes or objects of interest.

The term "depth of field" refers to the distance between the nearest and farthest objects in a scene that appear acceptably sharp in an image. Although a lens can precisely focus at only one distance at a time, the decrease in sharpness is gradual on each side of the focused distance, so that within the depth of field, the amount of unsharpness is imperceptible under normal viewing or imaging conditions. All objects within the depth of field of an imaging or optical system are considered to be in focus.

The term "Hadamard multiplication" refers to a type of matrix multiplication where the matrices being multiplied have the same number of rows and columns, as does the resultant or output matrix, and the elements of the resultant or output matrix, for a specific row and column, are formed by the multiplication of the values of the elements having the same specific row and column. This is also known as element-by-element matrix multiplication.

The term "duty cycle" refers to the time that an entity spends in an active state as a fraction of the total time under consideration. For a light emitting diode (LED), the duty cycle would be the fraction of the time that the LED has actually been emitting light since a predetermined starting time. The amount of time that an LED has actually been emitting light is the numerical value of the duty cycle (a number between 0.0 and 1.0) times the time elapsed since the predetermined starting time.

The term "diagnostic cassette" refers to test elements that are commonly defined by a flat planar substrate having a plurality of transparent microtubes or microcolumns that define test chambers. A predetermined quantity of inert bead or gel material is added to each of the microtubes. This inert material may be coated with an antibody or an antigen or provided with a carrier-bound antibody or antigen or with specific reagents. Typically, a foil wrap is used to cover the top of the card or cassette, thereby sealing the contents of each microcolumn until the time of test. The foil wrap is pierceable or otherwise removed to enable aliquots of patient sample and/or reagents to be added to each of the microtubes, either manually or in an automated apparatus.

The term "diagnostic analyzer" or "diagnostic clinical analyzer" refers to a semi-automated or automated apparatus composed of various subsystems including a patient sample handler, a test vessel (such as a diagnostic cassette) handler, an incubator, a centrifuge, a pipette for obtaining and dispensing reagents and patient samples, and a means to measure and quantify the result of specific tests on the patient sample among others.

One aspect of the invention is directed to a method and apparatus for producing color digital images at full resolution using a gray-scale digital camera or sensor 100. A primary benefit of the technology is reduced unit manufacturing cost in comparison to the use of a color digital camera or sensor, producing equivalent digital resolution, when employed as a component of a diagnostic clinical analyzer. Another benefit is that the resulting color image quality produced by this method using the gray-scale digital camera or sensor 100 is of higher quality than an image produced by a color digital camera or sensor, of equivalent spatial resolution, employing a color filter array because of the loss of effective resolution (resulting in reduced resolution) due to the image sensor data manipulation required in the latter case. Color filter arrays are described by Bryce E. Bayer in U.S. Pat. No. 3,971,065 entitled "Color imaging array" which is hereby incorporated by reference in its entirety. Yet another benefit is that the smaller physical size of the gray-scale digital camera or sensor 100, as compared to the size of a color digital camera or sensor of equivalent resolution, results in a shorter optical path more suitable for confined spaces. The process of producing a diagnostic result generally requires the transport of the diagnostic cassette to accept the patient sample and diagnostic reagents plus potential movement to a region of higher temperature (incubation) or to an apparatus to apply centrifugal force. At the end of the incubation and centrifugation processes, the diagnostic cassette or object of interest 102 can be held in one or more fixed positions. At that point, sequential illumination can be employed to obtain a full resolution color digital image of the front and of the back of the diagnostic cassette or object of interest 102 and its contents.

Figure 1:
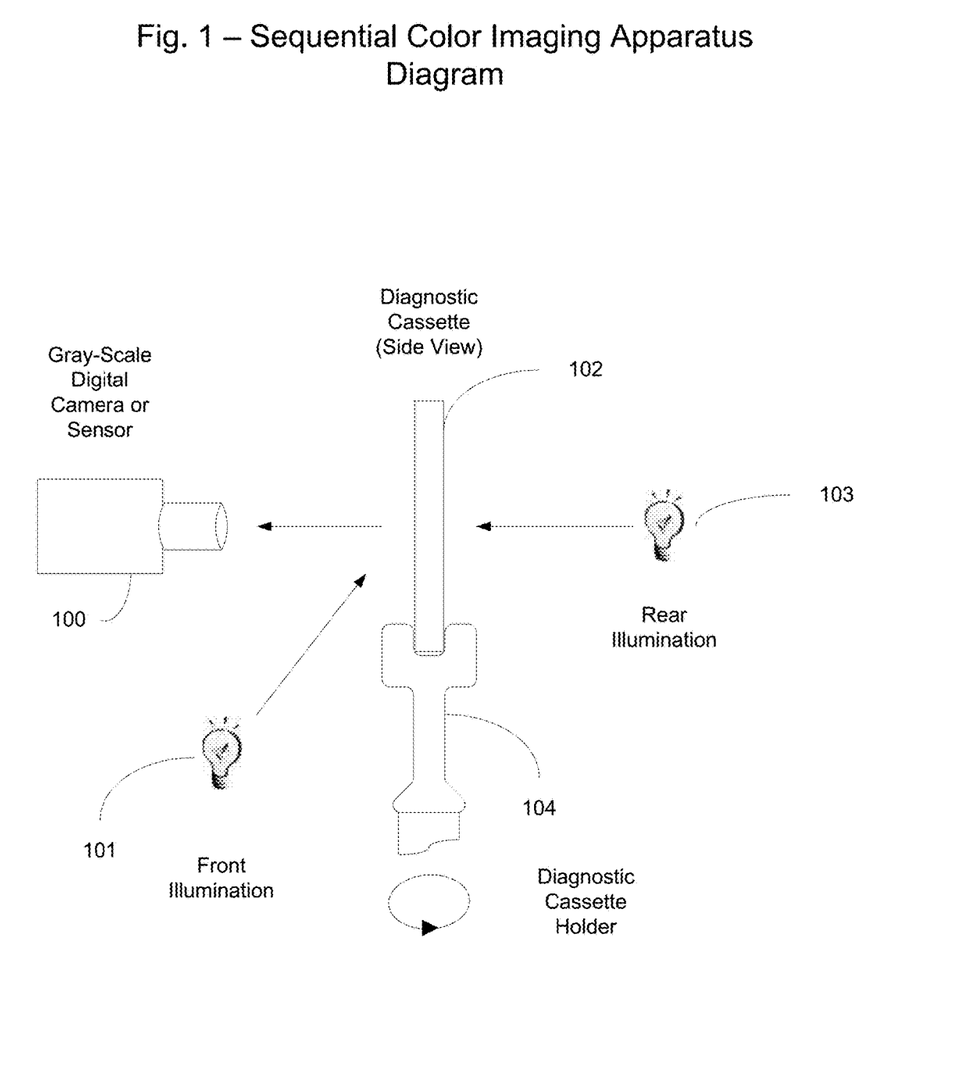
FIG. 1 is a schematic diagram of a sequential color imaging apparatus consisting of a gray-scale digital camera or sensor 100, a front tri-color illumination source 101, a diagnostic cassette or object of interest 102, a back or rear tri-color illumination source 103, and a mechanical means 104 to hold and manipulate the diagnostic cassette or object of interest 102.

FIG. 1 is a simplified schematic diagram of the sequential color imaging apparatus. Conceptually, a gray-scale digital camera or sensor 100 receives light, at any specific instance in time, of only one color from at least one front illumination light source, preferably tri-color light emitting diodes (LEDs) 101, which can selectively emit red, green, or blue light and from at least one rear illumination source, preferably tri-color light emitting diodes (LEDs) 103, which can selectively emit red, green, or blue light. The illumination sequence of the tri-color LEDs is coordinated such that sequential monochrome exposures composed of only red, green, or blue light are produced. The mechanical holder 104 in FIG. 1 holds the diagnostic cassette or object of interest 102 while the sequential illumination and image capture for the front-side of the diagnostic cassette or object of interest 102 is in process. As the diagnostic cassette or object of interest 102 has two sides, the mechanical holder 104 is capable of rotating 180° so that the back-side of the diagnostic cassette or object of interest 102 can be imaged. As a result of the sequential illumination and image capture for the front-side of the diagnostic cassette or object of interest 102 and the sequential illumination and image capture for the back-side of the diagnostic cassette or object of interest 102, six images or image planes are produced, specifically:
  1. a monochrome red image of the front of the diagnostic cassette or object of interest 102.
  2. a monochrome green image of the front of the diagnostic cassette or object of interest 102.
  3. a monochrome blue image of the front of the diagnostic cassette or object of interest 102.
  4. a monochrome red image of the back of the diagnostic cassette or object of interest 102.
  5. a monochrome green image of the back of the diagnostic cassette or object of interest 102.
  6. a monochrome blue image of the back of the diagnostic cassette or object of interest 102.

Further details of a preferred mechanical holder 104 can be found in the commonly assigned co-pending application of Robert Jones and Lynn Willett entitled "An Apparatus for Gripping and Holding Diagnostic Cassettes" (Ser. No. 61/545,651), filed Oct. 11, 2011, which is hereby incorporated by reference in its entirety.

Figure 2:
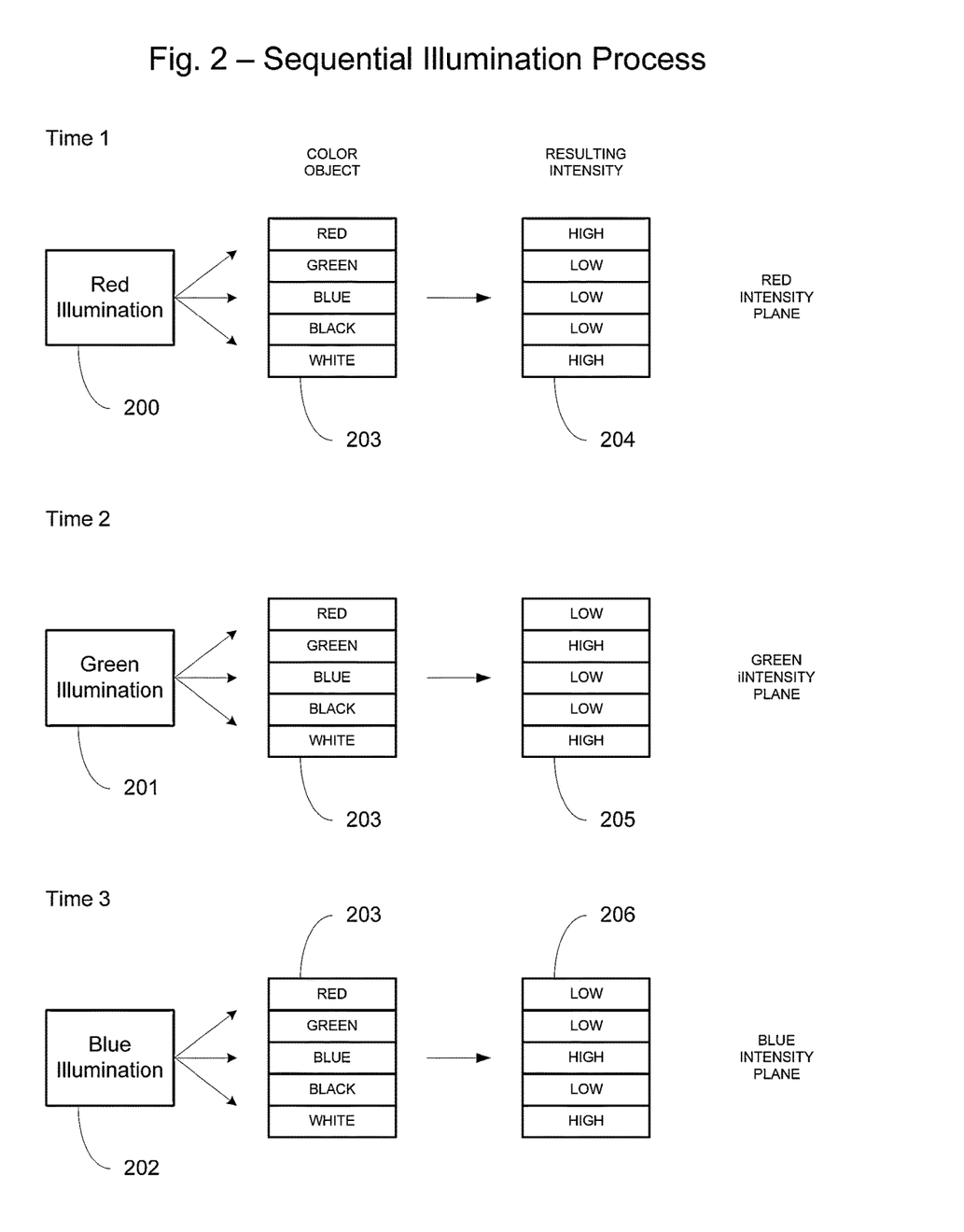

FIG. 2 is a schematic diagram depicting the qualitative aspects of the sequential exposure and imaging process. At Time 1, a combination red light source 200, from both the front illumination LED 101 and the rear illumination LED 102, is used to illuminate a color object 203 consisting of red, green, blue, black, and white patches. By definition, a patch exhibiting the color red is one which absorbs all wavelengths of light except red. Similarly, a green patch absorbs all wavelengths of light except green and a blue patch absorbs all wavelengths of light except blue. A black patch absorbs all wavelengths of light and reflects none whereas a white patch absorbs no wavelengths of light and reflects all. Hence, qualitatively, the resulting combination of reflectance and transmittance intensities 204 (represented here by a vector of five qualitative values) for red illumination 200 of the color object 203 results in a HIGH intensity for the red patch, LOW intensity for the green patch, LOW intensity for the blue patch, LOW intensity for the black patch, and HIGH intensity for the white patch. At Time 2, a green light source 201, from both the front illumination LED 101 and the rear illumination LED 102, is used to illuminate the color object 203. Qualitatively, the resulting combination of reflectance and transmittance intensities 205 (represented here by a vector of five qualitative values) for green illumination 201 of the color object 203 results in a LOW intensity for the red patch, HIGH intensity for the green patch, LOW intensity for the blue patch, LOW intensity for the black patch, and HIGH intensity for the white patch. At Time 3, a blue light source 202, from both the front illumination LED 101 and the rear illumination LED 102, is used to illuminate the color object 203. Qualitatively, the resulting combination of reflectance and transmittance intensities 206 (represented here by a vector of five qualitative values) for blue illumination 102 of the color palette 103 results in a LOW intensity for the red patch, LOW intensity for the green patch, HIGH intensity for the blue patch, LOW intensity for the black patch, and HIGH intensity for the white patch. Each set of these resulting intensities can be thought of as a color plane of intensities based upon red, green, and blue illumination, respectively.

Figure 3:
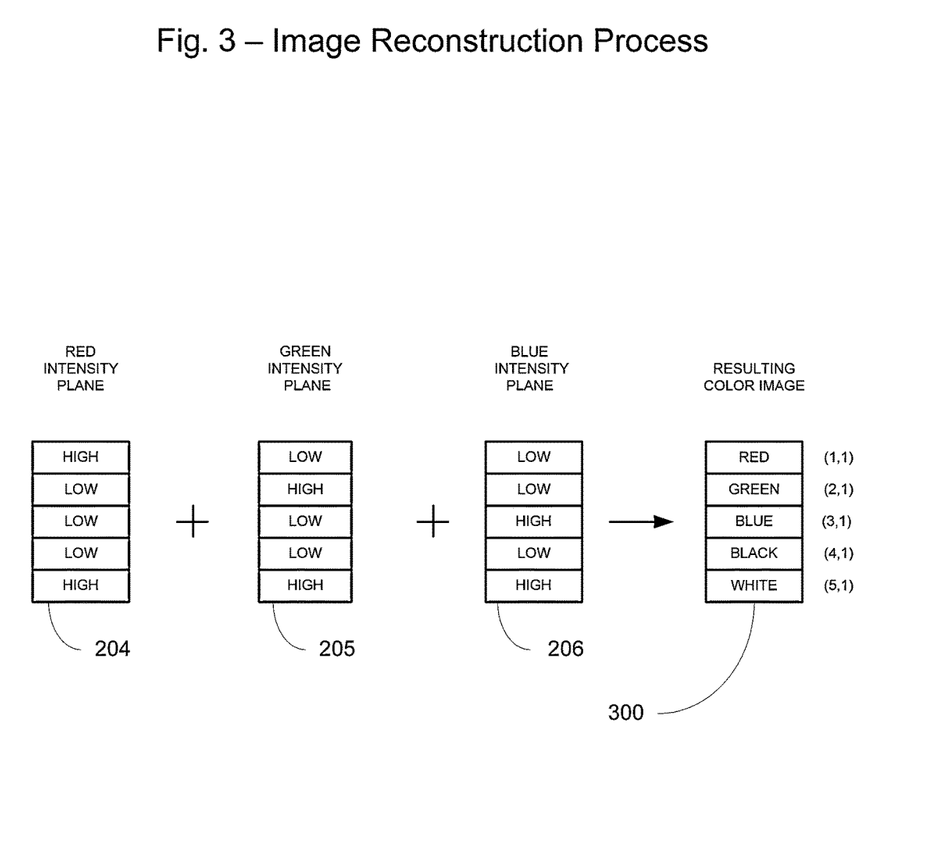

FIG. 3 is a diagram of the color image reconstruction process using the color planes resulting from the illumination operations as described in FIG. 2 above. The intensity resulting from a specific patch (or equivalently, a specific pixel) in the red color plane 204 is combined with intensities for the same patch (or equivalently, the same specific pixel) in the green color plane 205 and the blue color plane 206. Using qualitative measures of HIGH and LOW, for the first patch in the color planes (denoted element 1,1), the resulting color of the patch in the color image 300 requires the combination of HIGH red, LOW green, and LOW blue intensities resulting in a red patch in the color image 300. In a similar fashion, for the second patch in the color planes, (denoted element 2,1), the resulting color of the patch in the color image 300 requires the combination of LOW red, HIGH green, and LOW blue resulting in a green patch in the color image 300. Likewise, for the third patch in the color planes, (denoted element 3,1), the resulting color of the patch in the color image 300 requires the combination of LOW red, LOW green, and HIGH blue resulting in a blue patch in the color image 300. For the fourth patch in the color planes, (denoted element 4,1), the resulting color of the patch in the color image 300 requires the combination of LOW red, LOW green, and LOW blue resulting in a black patch in the color image 300. And for the fifth patch in the color planes, (denoted element 5,1), the resulting color of the patch in the color image 300 requires the combination of HIGH red, HIGH green, and HIGH blue resulting in a white patch in the color image 300.

Figure 4:
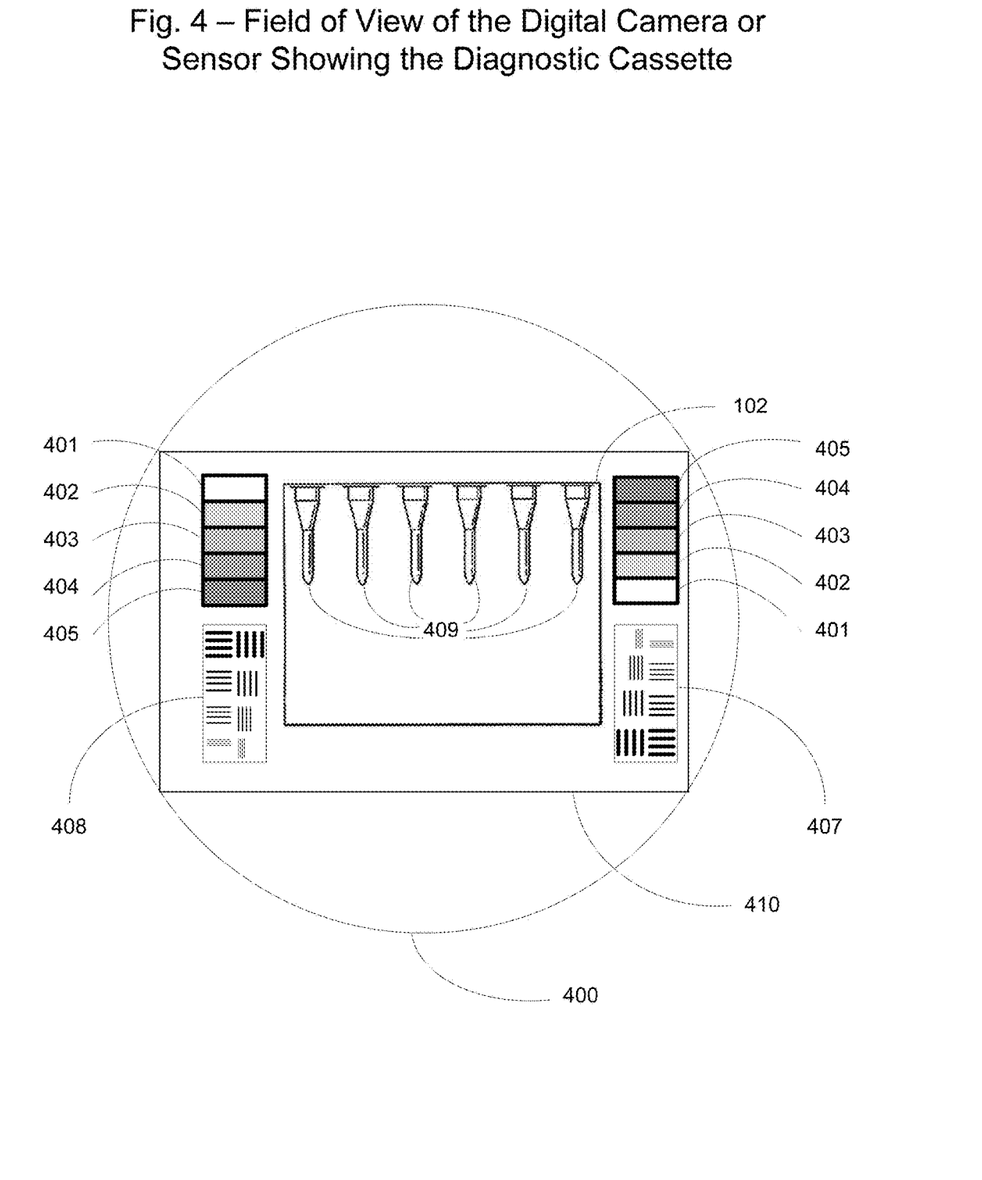
FIG. 4 is a diagram of a diagnostic cassette field of view 400 from the perspective of the gray-scale digital camera or sensor 100. In the field of view are gray-scale patches on plastic of 100% transmission intensity 401, 85% transmission intensity 402, 70% transmission intensity 403, 55% transmission intensity 404, 40% transmission intensity 405, and the diagnostic cassette or object of interest 102. This diagnostic cassette or object of interest 102 contains a number of microcolumns 409 containing gel or glass bead microparticles. Also in the field of view are a resolution target 407 on plastic and an inverted resolution target 408 on plastic. The area imaged by the gray-scale digital camera or sensor 100 is denoted by the rectangular region 410.

FIG. 4 is a diagram of the field of view 400 of the digital camera or sensor 100 showing the diagnostic cassette or object of interest 102, upright 407 and inverted 408 resolution targets, and gray-scale test patches (401, 402, 403, 404, and 405). The upright 407 and inverted 408 resolution targets and the gray-scale test patches (401, 402, 403, 404, and 405) are presented on a clear plastic pane in the background of the diagnostic cassette or object of interest 102. There are two groups of gray-scale patches, one on each side of the diagnostic cassette or object of interest 102. On the left hand side, from top to bottom, there is gray-scale patch of 100% transmission intensity 401, 85% transmission intensity 402, 70% transmission intensity 403, 55% transmission intensity 404, and 40% transmission intensity 405. On the right hand side, from top to bottom, there is gray-scale patch of 40% transmission intensity 405, 55% transmission intensity 404, 70% transmission intensity 403, 85% transmission intensity 402, and 100% transmission intensity 401. These gray-scale patches are used to calibrate the images and establish an appropriate white/color balance. The upright 407 and inverted 408 resolution targets are used to make sure that the diagnostic cassette or object of interest 102 is in focus. Both the upright 407 and inverted 408 resolution targets and the diagnostic cassette or object of interest 102 are positioned such that they are included within the depth of field of the imaging system. Note that there are a number of microcolumns 409, containing gel or glass bead microparticles, which is where the solutions to be analyzed are placed.

Figure 5:
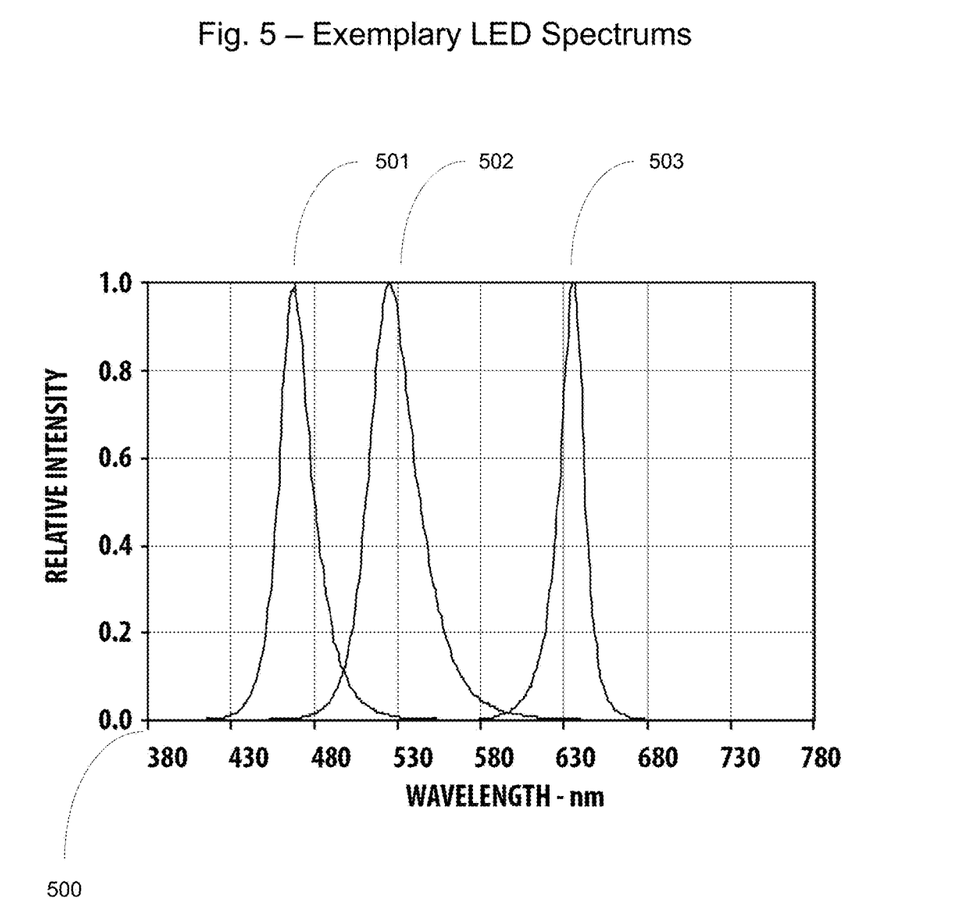
FIG. 5 is a graph 500 of exemplary spectrums of a tri-color light emitting diode (LED) emitting blue 501, green 502, and red 503 light.

FIG. 5 is a graph 500 of exemplary spectrums of blue light 501, green light 502, and red light 503 as emitted by tri-color LEDs. The peak value of relative intensity of each exemplary light spectrum has been normalized to unity for this graph.

Figure 6:
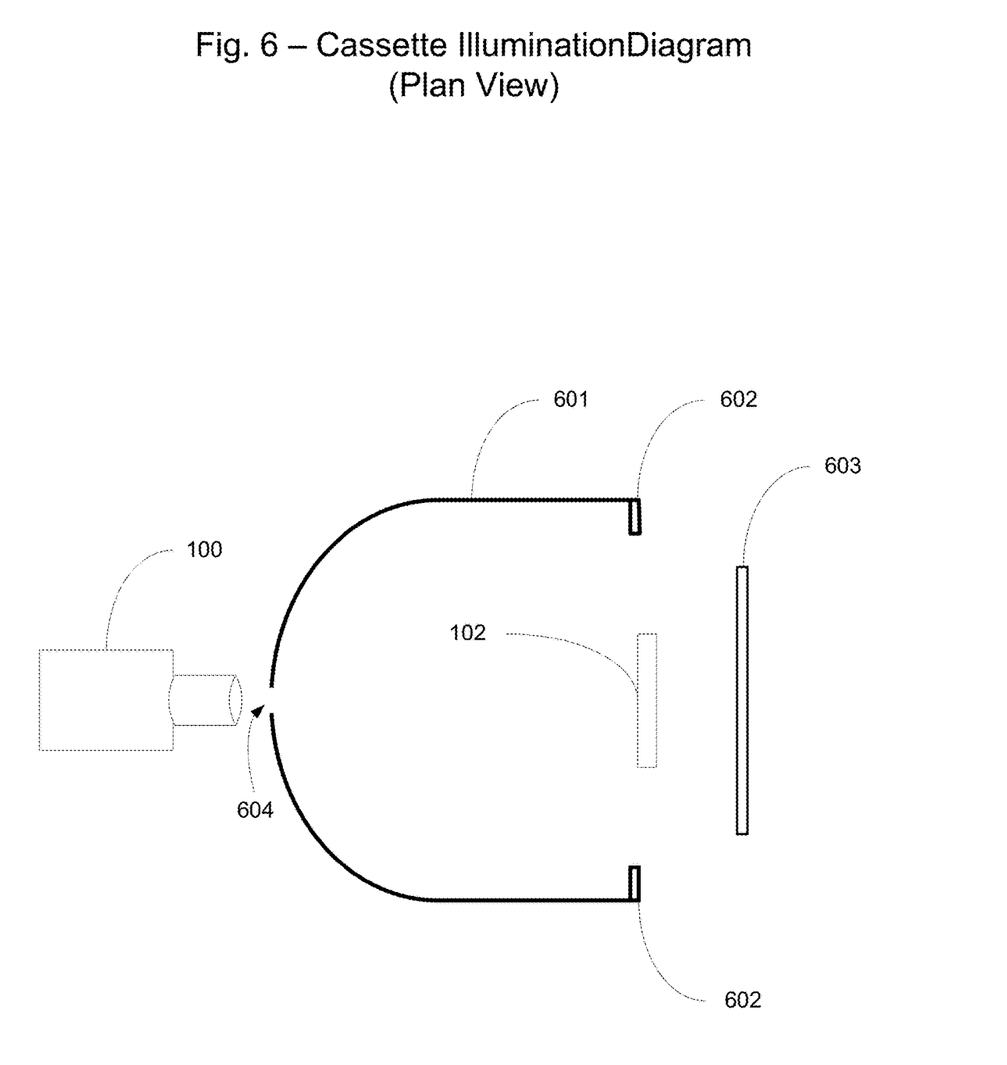
FIG. 6 is a plan diagram of the front illumination, back illumination and curved reflector employed to obtain uniform illumination of the diagnostic cassette or object of interest 102. The gray-scale digital camera or sensor 100 obtains an image through a hole in the curved reflector 601. Uniform illumination of the diagnostic cassette or object of interest 102 is provided by a set of front illumination light emitting diodes 602 and by a back illumination panel 603.

FIG. 6 is a more detailed schematic plan diagram of the imaging system shown in FIG. 1. The gray-scale digital camera or sensor 100 is shown behind a cylindrical reflector 601 which directs the light emitted from the set of tri-color light emitting diode circuit boards 602 mounted on the far right edges of the cylindrical reflector 601 onto the front of diagnostic cassette or object of interest 102. The rear illuminating light emitting diode circuit board 603 illuminates the rear of the diagnostic cassette or object of interest 102 directly. The gray-scale digital camera or sensor 100 images the diagnostic cassette or object of interest 102 through an opening 604 in the cylindrical reflector 601. The light reaching the gray-scale digital camera or sensor 100 is a combination of light emitted by the set of front illumination light emitting diode circuit boards 602 and the rear illumination light emitting diode circuit board 603. The cylindrical reflector 601 directs the light being emitted by the set of front illumination light emitting diode circuit boards 602 towards the front of the diagnostic cassette or object of interest 102. This illumination along with illumination from the rear illumination light emitting diode circuit board 603 provides uniform illumination intensity.

Figure 7:
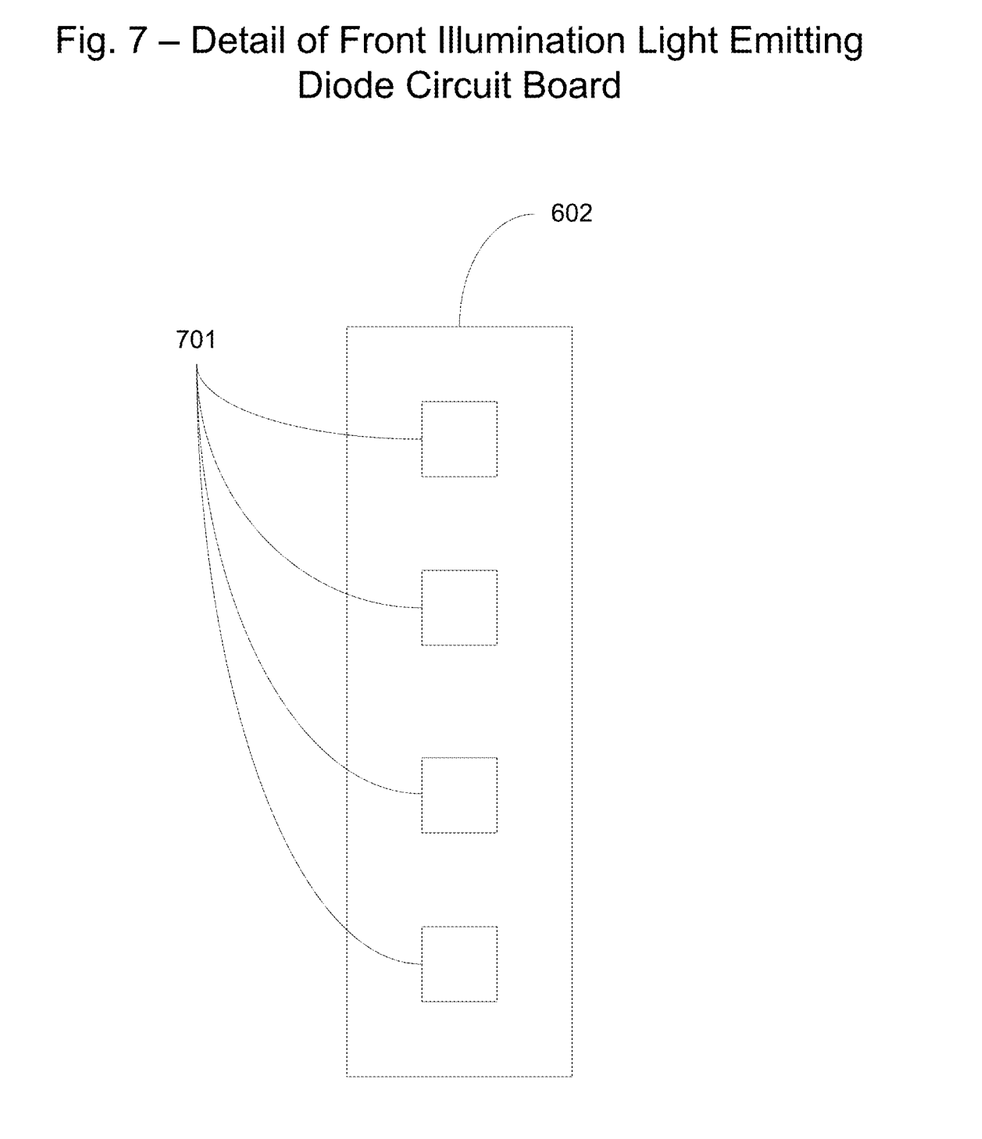
FIG. 7 is a diagram of details of the front illumination light emitting diode circuit board 602 showing four tri-color light emitting diodes 701 vertically aligned.

FIG. 7 is a schematic diagram of one of the set of two front illumination light emitting diode circuit boards 602. The circuit board 602 has a vertical to horizontal aspect ratio of substantially between 3 to 1 and 10 to 1. The tri-color light emitting diodes 701 are distributed vertically. While four tri-color light emitting diodes, arranged in a vertical pattern, are shown in FIG. 7, configurations having from substantially 2 to 12 vertically aligned light emitting diodes are possible.

Figure 8:
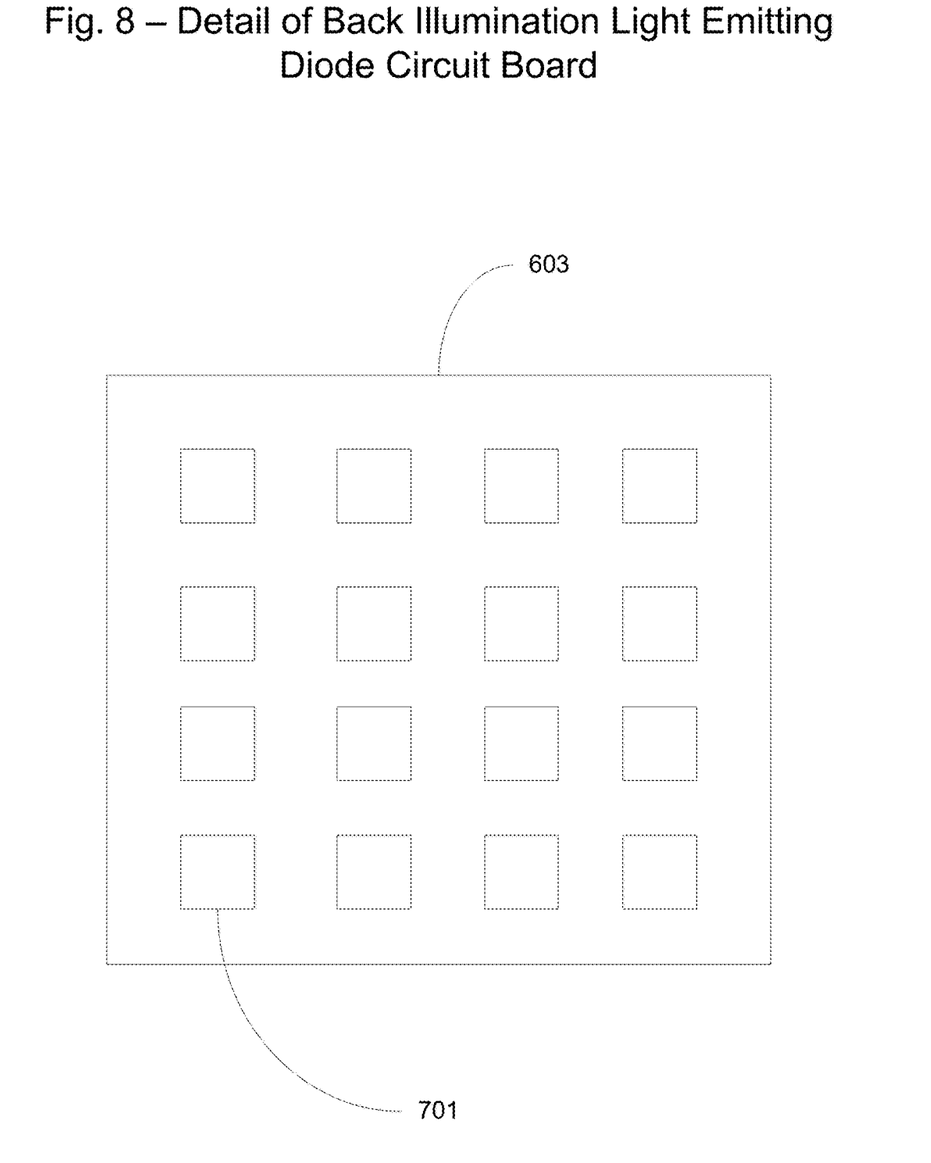
FIG. 8 is a diagram of the details of the back illumination light emitting diode circuit board 603 showing four rows and four columns for tri-color light emitting diodes 701 aligned in a square pattern.

FIG. 8 is a schematic diagram of the back illumination light emitting diode circuit board 603. The circuit board 603 is substantially rectangular in shape with tri-color light emitting diodes 701 configured in a substantially rectangular pattern or array. The circuit board 603 shown in FIG. 8 has 16 tri-color light emitting diodes 701 configured in a substantially rectangular array; however, different patterns or arrays of tri-color light emitting diodes 701 is possible including having different numbers of diodes 701 in either the horizontal (row) or vertical (column) orientations. Additionally, it is possible to have a smaller number or a larger number overall of diodes 701, substantially in the range of 9 to 144.

Figure 9:
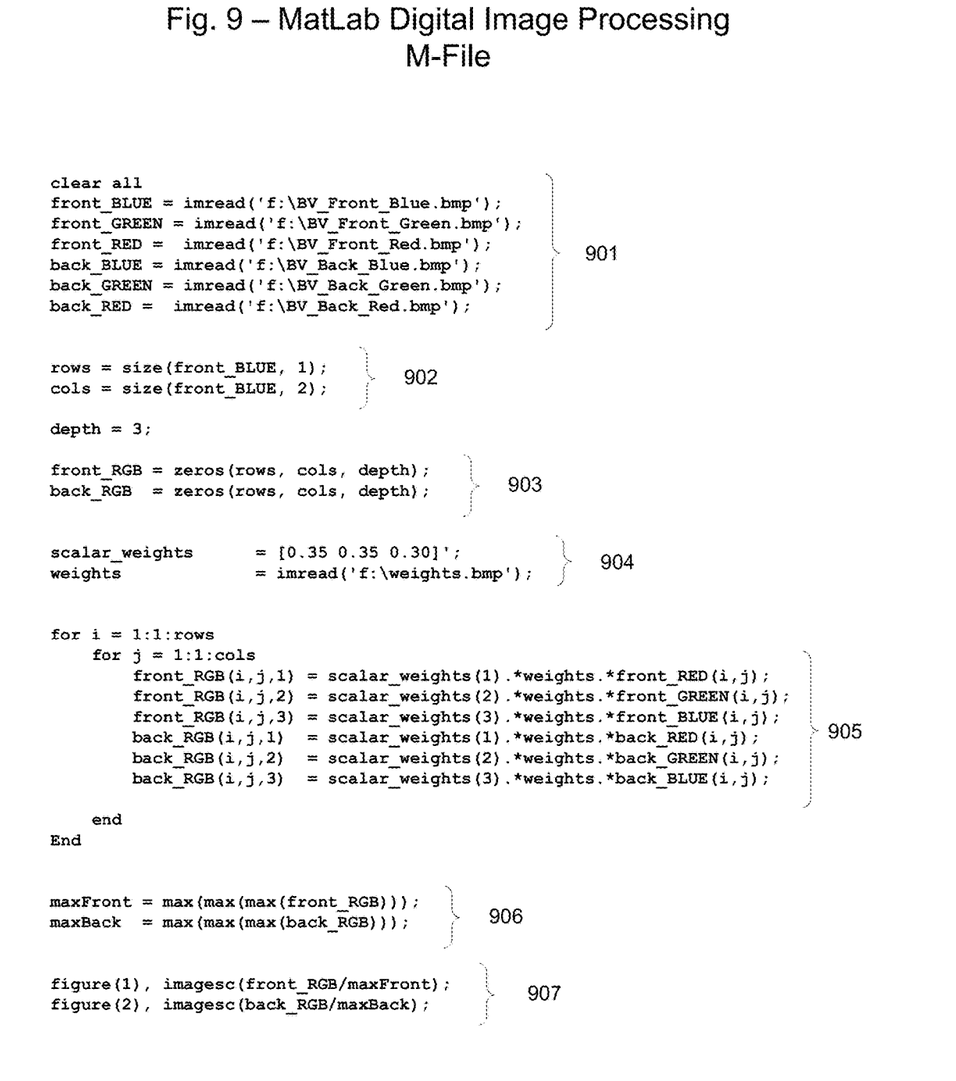
FIG. 9 is a listing of exemplary MatLab source code used to implement post sequential illumination exposure digital image processing including illumination intensity correction, gain correction, and construction of the final composite color (which approximates the visual response of a human observer) front and back images of the diagnostic cassette or object of interest.

FIG. 9 is a listing of an example MatLab M-File used to calibrate, process, and produce the final front illumination and back illumination full color images obtained from the red, green, and blue monochrome sequential exposures. The output from the gray-scale digital camera or sensor 100, in bit map format, is read into MatLab from an image storage area on file f: in statements 901. Note that there are red, green, and blue monochrome planes for each front illumination exposure and for each back illumination exposure. The size of each digital image, both front illumination and back illumination, is determined in statements 902. Statements 903 secure space to store the output of the computations and initialize all elements of that space to zeros. The scalar weights for each color plane are defined in statement 904. Statements 905 apply the appropriate scalar weight to element in the six image planes, respectively. A maximum intensity value for the front illumination plane and a maximum intensity value for the back illumination plane are found in statements 906. These maximum intensity values are then used to scale the final front illumination image and the back illumination image in statement 907. Note that a correction or calibration weight matrix has been employed in this computation.

The above apparatus is appropriately configured to allow for a calibration and image processing method capable of coping with a number of environmental and equipment-related issues. These issues are most conveniently organized into four tiers as follows:

Tier 1: Electrical Component Variability
    Variations in gray-scale digital camera or sensor sensitivity including illumination variability
Tier 2: Variations in ambient lighting
    Variations in input power
    Obtaining required front to back image contrast
Tier 3: Electrical component degradation over time
    Electrical component temperature sensitivity
    Output image color requirements
Tier 4: Component changes due to replacement or due to a change
    in component manufacturer
Imaging Subsystem Calibration A tier 1 calibration of the imaging subsystem takes place shortly after manufacture in the factory. Electrical component variability is addressed via the use of mechanically modifiable resistors (for example, a potentiometer which is a three-terminal resistor with a sliding contact that forms an adjustable voltage divider) and instrumentation such that a sequence of predefined test signals results in a sequence of predefined test results. Variations in gray-scale digital camera or sensor 100 sensitivity including illumination variability are addressed via the determination of a matrix of multiplicative weights. This matrix of multiplicative weights has the same row and column dimensions as the output matrix of pixels from the digital camera or sensor 100 such that a specific weight is applied to a specific image via Hadamard multiplication.

A tier 2 calibration takes place when the diagnostic analyzer is moved to its production location. Variations in input power are managed via the use of a Texas Instruments TLC5923 integrated circuit (for details see, Kouzo Ichimaru, "Temperature compensated constant-voltage circuit and temperature compensated constant-current circuit," U.S. Pat. No. 5,430,395 which is hereby incorporated by reference in its entirety) which implements a temperature compensated constant current circuit that also incorporates error information circuitry allowing the detection of broken or disconnected LED devices. Obtaining the required front to back image contrast is obtained by adjusting the relative amount of power sent to the front and back front illumination light emitting diode circuit boards, 602 and 603, respectively. Based upon the green image, the ratio of the average intensity of the front illuminated image compared to the average intensity of the back illuminated image is set to a predetermined value. This provides the required front to back contrast. Variations in gray-scale digital camera or sensor 100 sensitivity including illumination variability are addressed by repeating the tier 1 calibration obtaining a new matrix of multiplicative weights. This compensates for variations in gray-scale digital camera or sensor 100 sensitivity including illumination variability and also compensates for variations in ambient lighting plus any variations in illumination intensity caused by the first two steps of the tier 2 calibration procedure.

A tier 3 calibration or more precisely, compensation for electrical component degradation over time is achieved by exploiting known hardware behavior. For example, it is well known that light emitting diodes produce less light output per unit input power as a function of the number of hours of use. In particular, this decrease in light output as a function of the cumulative time the diode has been emitting light, based on the duty cycle, can be modeled and used to obtain a first order image correction matrix to maintain the imaging subsystem in calibration over a longer time span. The image correction matrix elements would vary as a function time depending upon the total number of hours that the LED has been emitting light. For details, see Anthony P. Zygmunt, Chein Hsun Wang, and J. Anthony Spies "System and Method for LED Degradation and Temperature Compensation," US 2010/0007588 which is hereby incorporated by reference in its entirety. Compensation for electrical component temperature sensitivity is achieved via the Texas Instrument TLC5923 integrated circuit as referenced above.

A tier 4 calibration consists of performing tier 1, tier 2, and tier 3 calibrations again in sequence.

Image Processing and Reconstruction Procedure

Generally occurs after all calibration procedures have been executed and is the normal operating mode of the imaging subsystem.

The prior qualitative discussion of FIGS. 2 and 3 can be made quantitative by the introduction of numerical values for intensity. It is common for a byte or eight bits of a computer word to represent the intensity value of a pixel. This allows for:

$$2^8=256$$

intensity levels in the range of [0, 255]. It is also common to describe the range of intensity using a floating point number in the range of [0.0, 1.0] as employed in MatLab. This latter construct will be used in describing the following preferred method. Note that the exemplary image sizes used in the following examples is much smaller than real images that may have many thousands of rows and columns.

Consider the following example image in matrix form:

$$A = \begin{pmatrix} R & R & R & R & R & R & R & R & R & R \\ R & R & R & R & R & R & R & R & R & R \\ G & G & G & G & G & G & G & G & G & G \\ G & G & G & G & G & G & G & G & G & G \\ B & B & B & B & B & B & B & B & B & B \\ B & B & B & B & B & B & B & B & B & B \\ K & K & K & K & K & K & K & K & K & K \\ K & K & K & K & K & K & K & K & K & K \\ W & W & W & W & W & W & W & W & W & W \\ W & W & W & W & W & W & W & W & W & W \end{pmatrix}$$

Where there are two rows of red pixels (R), two rows of green pixels (G), two rows of blue pixels (B), two rows of black pixels (K), and two rows of white pixels (W). Upon exposure to red, green, or blue wavelength light, the reflection intensity of the above image will be recorded as a 10×10 matrix of values in the closed interval [0.0, 1.0]. For example, a uniform exposure to green wavelength light of intensity 0.8 would ideally produce the following green image plane, in reflection intensities, for a gray-scale digital camera or sensor 100:

$$A_{GREEN} = \begin{pmatrix} 0.0 & 0.0 & 0.0 & 0.0 & 0.0 & 0.0 & 0.0 & 0.0 & 0.0 & 0.0 \\ 0.0 & 0.0 & 0.0 & 0.0 & 0.0 & 0.0 & 0.0 & 0.0 & 0.0 & 0.0 \\ 0.8 & 0.8 & 0.8 & 0.8 & 0.8 & 0.8 & 0.8 & 0.8 & 0.8 & 0.8 \\ 0.8 & 0.8 & 0.8 & 0.8 & 0.8 & 0.8 & 0.8 & 0.8 & 0.8 & 0.8 \\ 0.0 & 0.0 & 0.0 & 0.0 & 0.0 & 0.0 & 0.0 & 0.0 & 0.0 & 0.0 \\ 0.0 & 0.0 & 0.0 & 0.0 & 0.0 & 0.0 & 0.0 & 0.0 & 0.0 & 0.0 \\ 0.0 & 0.0 & 0.0 & 0.0 & 0.0 & 0.0 & 0.0 & 0.0 & 0.0 & 0.0 \\ 0.0 & 0.0 & 0.0 & 0.0 & 0.0 & 0.0 & 0.0 & 0.0 & 0.0 & 0.0 \\ 0.8 & 0.8 & 0.8 & 0.8 & 0.8 & 0.8 & 0.8 & 0.8 & 0.8 & 0.8 \\ 0.8 & 0.8 & 0.8 & 0.8 & 0.8 & 0.8 & 0.8 & 0.8 & 0.8 & 0.8 \end{pmatrix}$$

However, achieving a uniform exposure is difficult and there could be, for example, a gradient in exposure from left to right which might produce the following green image plane:

$$A_{GREEN\ MEASURED} =$$

$$\begin{pmatrix} 0.0 & 0.0 & 0.0 & 0.0 & 0.0 & 0.0 & 0.0 & 0.0 & 0.0 & 0.0 \\ 0.0 & 0.0 & 0.0 & 0.0 & 0.0 & 0.0 & 0.0 & 0.0 & 0.0 & 0.0 \\ 0.8 & 0.75 & 0.70 & 0.65 & 0.60 & 0.55 & 0.50 & 0.45 & 0.40 & 0.35 \\ 0.8 & 0.75 & 0.70 & 0.65 & 0.60 & 0.55 & 0.50 & 0.45 & 0.40 & 0.35 \\ 0.0 & 0.0 & 0.0 & 0.0 & 0.0 & 0.0 & 0.0 & 0.0 & 0.0 & 0.0 \\ 0.0 & 0.0 & 0.0 & 0.0 & 0.0 & 0.0 & 0.0 & 0.0 & 0.0 & 0.0 \\ 0.0 & 0.0 & 0.0 & 0.0 & 0.0 & 0.0 & 0.0 & 0.0 & 0.0 & 0.0 \\ 0.0 & 0.0 & 0.0 & 0.0 & 0.0 & 0.0 & 0.0 & 0.0 & 0.0 & 0.0 \\ 0.8 & 0.75 & 0.70 & 0.65 & 0.60 & 0.55 & 0.50 & 0.45 & 0.40 & 0.35 \\ 0.8 & 0.75 & 0.70 & 0.65 & 0.60 & 0.55 & 0.50 & 0.45 & 0.40 & 0.35 \end{pmatrix}$$

Such non-uniformities in exposure can be handled via the use of a green weight matrix whose numerical elements would have values determined by the calibration procedure that, once applied, would be capable of producing a corrected green color plane. For exposure gradients as in $A_{GREEN\ PRIME}$ above, the following green weight matrix (with numerical values to two decimal places) could be employed:

$$A_{GREEN\ WEIGHT} =$$

$$\begin{pmatrix} 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \\ 1.00 & 1.07 & 1.14 & 1.23 & 1.33 & 1.45 & 1.60 & 1.78 & 2.00 & 2.29 \end{pmatrix}$$

such that a corrected exposure matrix is obtained as follows:

$$A_{GREEN\ CORRECTED} = A_{GREEN\ WEIGHT}(\cdot *) A_{GREEN\ MEASURED}$$

where the operation ($\cdot *$) denotes the element-by-element multiplication of the matrix elements as defined in MatLab (See *Getting Started with MatLab* 7, September 2010, The Math Works, Inc., pages 2-24 and 2-25, which is hereby incorporated by reference in its entirety) and is also known as the Hadamard product. Note that for this particular example that $$A_{GREEN\ CORRECTED} = A_{GREEN}$$

to a couple of decimal places, that is to say that essentially perfect correction would be obtained.

In a similar manner, corrections for alternative exposure geometries can be implemented. As an additional example, suppose the green wavelength exposure was a point source such that maximum intensity from the source was directed to the center of the object being imaged. The point source exposure (in intensity) would then have a decreasing gradient, in a radial direction, to pixels at increasing distances from the center of the object being imaged. A weight matrix in this case would have the lowest numerical values at the center with increasing numerical values as a function of the distance from the center to compensate for the radial falloff in exposure intensity.

In addition to exposure geometry corrections, other digital image corrections such as compensation for the long-term degradation of output intensity of LEDs as a function of age and/or compensation for the spectral response or sensitivity of the gray-scale being employed. In any event, the resulting weight matrices can be combined into a single weight matrix to account for all corrections being employed as follows:

$$A_{WEIGHT} = A_{CORRECTION\#1}(\cdot *) A_{CORRECTION\#2}(\cdot *) A_{CORRECTION\#3}$$

where the ($\cdot *$) operation denotes the multiplication of the $A_{GREEN\ GAIN}$ scalar by each element of the resulting Hadamard matrix multiplication on the right. Further corrections are also possible, for example, it is possible that both the peak relative intensity and the area under the relative intensity response or sensitivity curve could vary significantly as a function of light wavelength. Hence, for a specific intensity exposure, the reflection intensity of red might only be a fraction of the reflection intensity of green or blue. Likewise, for a gray-scale digital camera or sensor 100, the spectral response or sensitivity to red light might also only be a fraction of the reflection intensity of green or blue. This variability is most easily compensated for by having a scalar gain correction for each wavelength exposure. Specifically, green exposure reflection intensity combined with a green spectral response or sensitivity of the gray-scale could be corrected by applying a gain scalar to the previously determined exposure correction equation for geometry as follows:

$$A_{GREEN\ TOTALLY\ CORRECTED} = A_{GREEN\ GAIN}(\cdot *) A_{GREEN\ WEIGHT}(\cdot *) A_{GREEN\ MEASURED}$$

where the ($\cdot *$) operation denotes the multiplication of the $A_{GREEN\ GAIN}$ scalar by each element of the resulting Hadamard matrix multiplication on the right. In aggregate, the correction processing is carried out plane-wise as follows:

$$A_{RED\ TOTALLY\ CORRECTED} = A_{RED\ GAIN}(*) A_{RED\ WEIGHT}(\cdot *) A_{RED\ MEASURED}$$

$$A_{GREEN\ TOTALLY\ CORRECTED} = A_{GREEN\ GAIN}(*) A_{GREEN\ WEIGHT}(\cdot *) A_{GREEN\ MEASURED}$$

$$A_{BLUE\ TOTALLY\ CORRECTED} = A_{BLUE\ GAIN}(*) A_{BLUE\ WEIGHT}(\cdot *) A_{BLUE\ MEASURED}$$

It will be apparent to those skilled in the art that various modifications and variations can be made to the methods and processes of this invention. Thus, it is intended that the present invention cover such modifications and variations, provided they come within the scope of the appended claims and their equivalents.

The disclosure of all publications cited above is expressly incorporated herein by reference in their entireties to the same extent as if each were incorporated by reference individually.

We claim:

1. An apparatus for the construction of a color digital image of an object of interest comprising:
   a gray-scale digital camera or sensor capable of generating a plurality of gray-scale images while the object of interest is illuminated with lights having different wavelengths,
   a mechanical means to hold said object of interest with respect to the gray-scale digital camera or sensor,
   a source of front illumination capable of multiple illuminations of said object of interest with red, green, and blue wavelength light, a source of rear illumination capable of multiple illuminations of said object of interest with red, green, and blue wavelength light, and a means to construct a color digital image of said object of interest by combining color plane data created from the plurality of gray-scale images viewed by the gray-scale digital camera or sensor, wherein said means is in electrical contact with said gray-scale digital camera or sensor.

2. The apparatus of claim 1, wherein the means to construct a color digital image is an electric circuit containing at least one application-specific integrated circuit.

3. The apparatus of claim 1, wherein the means to construct a color digital image is an electric circuit containing at least one field-programmable gate array.

4. The apparatus of claim 1, wherein the means to construct a color digital image is software in a general purpose digital computer.

5. The apparatus of claim 1, wherein the apparatus is an imaging subsystem for a diagnostic clinical analyzer.

6. The apparatus of claim 1, wherein the object of interest is a diagnostic cassette.

7. The apparatus of claim 1, wherein the constructed color digital image is of full resolution.

8. The apparatus of claim 1, wherein a cylindrical reflector in optical connection with said source of front illumination and in optical connection with said source of rear illumination provides uniform illumination to said object of interest.

9. The apparatus of claim 1, wherein said source of front illumination is provided by a plurality of light emitting diode circuit boards.

10. The apparatus of claim 1, wherein said source of rear illumination is provided by at least one light emitting diode circuit board.

11. The apparatus of claim 1, wherein the plurality of gray-scale images are composed exclusively of black, white, and shades of gray varying from black to white.

12. The apparatus of claim 1, wherein the color plane data includes varying reflection or transmission intensities or densities observed by the gray-scale digital camera or sensor while the object of interest is illuminated with lights having different wavelengths.

13. The apparatus of claim 1, wherein construction of the color digital image includes creation of a color plane from the color plane data from at least one of the plurality of gray-scale images, multiplication of the color plane by a pre-defined color weighting matrix to produce a weighted color plane, and multiplication of the weighted color plane by a pre-defined selected gain scalar to produce a final color plane.

* * * * *